United States Patent [19]

Mezick

[11] Patent Number: 4,487,782

[45] Date of Patent: Dec. 11, 1984

[54] TOPICAL TREATMENT OF NON-INFLAMMATORY ACNE

[75] Inventor: James A. Mezick, East Brunswick, N.J.

[73] Assignee: Ortho Pharmaceutical Corporation, Raritan, N.J.

[21] Appl. No.: 362,356

[22] Filed: Mar. 26, 1982

[51] Int. Cl.³ .............................................. A61K 31/19
[52] U.S. Cl. ..................................... 424/317; 424/344
[58] Field of Search ................................ 424/317, 344

[56] References Cited

FOREIGN PATENT DOCUMENTS 1335867 10/1973 United Kingdom .

OTHER PUBLICATIONS

Plewig et al., "Retinoids–Advances in Basic Research & Therapy", Ed. Orfanos et al., pp. 219–223 and 232–234, (7-29-81).
Gomez–"Retinoids–Advances in Basic Research and Therapy", Ed. Orfanos et al., pp. 213–217, (7-29-81).
Chemical Abstracts 93:37290r, (Gomez et al.), 1980.

Primary Examiner—Leonard Schenkman
Attorney, Agent, or Firm—Benjamin F. Lambert

[57] ABSTRACT

Topical treatment of non-inflammatory acne by the administration of 13-cis-retinoic acid is disclosed.

8 Claims, No Drawings

TOPICAL TREATMENT OF NON-INFLAMMATORY ACNE

BACKGROUND OF THE INVENTION

The present invention relates to a method of treating noninflammatory acne.

Acne vulgaris is a common dermatological disorder which affects large patient populations in the preadolescent, adolescent and young adult age groups. Since it occurs primarily in the face and trunk areas of the body, the condition probably causes more mental pain and anguish than many other diseases which have an affect on an individual's physical appearance. Two types of skin lesions are observed in acne vulgaris: (1) non-inflammatory lesions which include open (blackhead) and closed (whitehead) comedones and (2) inflammatory lesions which include papules and pustules. The most severe form of acne is known as acne conglobata or nodulocystic acne. Acne conglobata patients, in addition to having comedones, papules and pustules, suffer from large inflammatory nodules and draining sinuses.

Acne develops in the sebaceous follicle and is initiated by an abnormal keratinization process in which epithelial cells, keratin and sebum adhere together and become impacted forming the initial lesion in acne, the microcomedo. When the normal flow of sebum to the skin surface is blocked by the microcomedo, the follicle begins to enlarge and forms non-inflammatory open (blackhead) and/or closed (whitehead) comedones. The inflammatory phase of acne is initiated when the follicular epithelium surrounding the non-inflammatory comedones ruptures to form inflamed papules, pustules and cysts.

Therapy for non-inflammatory acne lesions generally involves local administration of an agent which causes an exfoliation of the follicular keratinous impaction and thereby exerts a comedolytic effect on comedones. All-trans-retinoic acid is a widely used topical comedolytic agent. Prolonged use of the compound, however, produces varying degrees of erythema and desquamation which are often accompanied by stinging and burning. Appropriate therapy for inflammatory lesions generally involves local and/or systemic administration of various agents. Topical pharmacologic agents which are used to treat inflamed pustules and papules include benzoyl peroxide and the tetracyclines. Oral erythromycin has also been shown to be useful in resolving inflammatory lesions.

The systemic administration of large doses of vitamin A (also known as retinol) have been reported to be useful in the treatment of acne (Straumford, J. V., "Vitamin A: Its Effect on Acne," Northwest Med., 42:219, 1943). More recently, Kligman et al. reported that large oral doses of vitamin A, 300,000 International Units and 500,000 International Units, were beneficial in the treatment of severe inflammatory acne (Kligman, A. M. et al., "Oral Vitamin A in Acne Vulgaris", Intl. J. Dermatol., 20:278, 1981.

The systemic administration of 13-cis-retinoic acid has been found to be effective when administered orally to patients with severe inflammatory cystic acne (Peck, G. L. et al., "Prolonged Remissions of Cystic Acne and Conglobate Acne with 13-Cis-Retinoic Acid", New Eng. J. Med., 300:329, 1979). In addition, oral administration of 13-cis-retinoic acid has been reported to be effective in the management of certain disorders of keratinization including basal cell carcinoma and keratoacanthoma (Haydey, R. P. et al., Treatment of Keratocanthomas With Oral 13-Cis-Retinoic Acid", New Eng. J. Med; 303, 1980). Topical administration of vitamin A acid has been reported by A. M. Kligman et al. to be effective in the treatment of open and closed comedones associated with acne ("Topical Vitamin A Acid in Acne Vulgaris", Arch. Derm. 99:469, 1969). The effectiveness of this treatment as disclosed by A. M. Kligman in U. S. Pat. No. 3,729,569 (Apr. 24, 1973) is apparently accompanied by the irritation effects associated with vitamin A acid.

Thus acne can be subdivided into two categories, inflammatory acne and non-inflammatory acne, based on both pathophysiological and therapeutic differences. Drugs that are effective, both orally and topically, in the treatment of inflammatory acne (e.g., benzoyl peroxide and the antibiotics) are clearly not effective in the treatment of comedogenic or non-inflammatory acne. On the other hand, drugs which have comedolytic activity (e.g., salicylic acid and all-trans vitamin A acid) and which are effective in treating non-inflammatory acne, are not effective in treating inflammatory acne.

SUMMARY OF THE INVENTION

The present invention describes a new therapeutic method for the treatment of non-inflammatory acne by the topical administration of 13-cis-retinoic acid. The unexpected result of this invention is that 13-cis-retinoic acid, unlike other oral treatments for inflammatory acne, is topically effective on non-inflammatory comedones. A second unexpected result of this invention is that 13-cis-retinoic acid, unlike all-trans-retinoic acid, exerts its topical anti-acne comedolytic effects while producing significantly less dermal irritation than the all-trans acid. It has now been shown that non-inflammatory acne can be effectively treated through repeated topical application of 13-cis-retinoic acid to the affected area.

The 13-cis-retinoic acid is preferably applied in a liquid composition. For example, the acid can be dissolved in small amounts in a water miscible (substantially oil- and fat-free) liquid having a high solvating action. A suitable solvent carrier consists essentially of a combination of from about 10–90% by weight of an alcohol such as ethyl alcohol or isopropyl alcohol and 90–10% by weight of a glycol such as propylene glycol or polyethylene glycol. Small amounts of other materials which do not materially alter the advantageous characteristics of the combination may also be included such as, for example, a small amount of polyethylene glycol 4000, which may be added to thicken the composition. An antioxidant, such as butylated hydroxytoluene or butylated hydroxyanisole, for example, may be included as a stabilizer to increase shelf life.

The concentration of 13-cis-retinoic acid in the composition is generally in the order of about 0.1% by weight of the applied composition. The 13-cis-retinoic acid concentration in the applied composition may range from 0.01% to 0.5% by weight, with a concentration in the range of from about 0.05 to about 0.25% being preferred.

The composition containing the 13-cis-retinoic acid is generally applied daily until the desired relief is obtained. This may require one or more applicaions a day, depending upon the particular individual being treated. The treatment normally requires about four to six weeks, however, severe cases of acne may require a much longer treatment. Although a liquid composition is the preferred carrier for the 13-cis-retinoic acid, ointment, cream and gel formulations may also be employed.

EXAMPLE 1

13-cis-Retinoic acid was evaluated for a reduction in size of horn-filled utriculi in the rhino mouse model system.* In this system, the dorsal trunk of the rhino mouse serves as the test site. The test compound was dissolved in alcohol:propylene glycol (70:30 v/v) and was topically applied from an automatic micropipette once daily, five consecutive days/week for two weeks. Following the last treatment (72 hours), the mice were sacrificed by cervical dislocation. The dorsal trunk skin was removed and placed into 0.5% acetic acid for approximately 18 hours at 4° C. to 6° C. The epidermis was then separated from the underlying dermis and processed by routine dehydration methods to permanent whole mounts to quantify utriculi diameters by microscopic examination. For each whole mount (one animal skin/slide), the diameter of ten utriculi in five random fields (N=50) was measured with an ocular micrometer.

*The skin of the rhino mouse, an allelic variant of the hairless mouse contains huge numbers of hornified utriculi which resemble comedones (S. Mann, Anat. Rec., 170:485, 1975; L. H. Kligman, et al. J. Invest. Dermatol, 73:354, 1979) and is a model system for the pharmacologic testing of agents for the treatment of acne (E. J. Van Scott, "Experimental Animal Integumental Models for Screening Potential Dermatologic Drugs", in: Advances in Biology of the Skin: Vol. XII, Pharmacology and the Skin, W. Montagna et al., Eds. New York, Meredith Corp., 1972, Chapter XXXIII). The results of these experiments are presented in Table I. As can be seen in Table 1, 13-cis-retinoic acid significantly reduced the size or horn-filled utriculi (comedones) in rhino mouse skin. In a comparative test a commercial topical antibiotic preparation used for the treatment of inflammatory acne, containing tetracycline hydrochloride, was inactive on rhino mouse skin.

TABLE 1

The Effect of Topically Applied 13-Cis-Retinoic Acid, and Tetracycline Hydrochloride on Reduction of Horn-Filled Utriculi (Comedones) in the Rhino Mouse

| Treatment | N | Concentration | Utriculus (Comedone) Diameter, microns ± SE | Percent Utriculus Reduction |
|---|---|---|---|---|
| Untreated | 4 | — | 186.5 ± 6.4 | — |
| 13-cis-retinoic acid | 5 | 0.05% | 121.6 ± 4.3 | 37.1 |
| Vehicle | 5 | — | 162.3 ± 8.4 | — |
| 13-cis- | 5 | 0.1% | 70.0 ± 2.2 | 56.9 |

TABLE 1-continued

The Effect of Topically Applied 13-Cis-Retinoic Acid, and Tetracycline Hydrochloride on Reduction of Horn-Filled Utriculi (Comedones) in the Rhino Mouse

| Treatment | N | Concentration | Utriculus (Comedone) Diameter, microns ± SE | Percent Utriculus Reduction |
|---|---|---|---|---|
| retinoic acid | | | | |
| Vehicle | 5 | — | 165.2 ± 2.9 | — |
| Tetracycline hydrochloride | 5 | 0.22% | 162.5 ± 10.3 | 1.63 |

In a 10-day repeat dose dermal irritation studies, the effects of twice daily application (single application 2-days) of 0.1% solution of 13-cis-retinoic acid, 0.1% solution of all-trans-retinoic acid and placebo vehicle (as in Example 1) to the shaved intact skin of mature albino rabbits were evaluated. Table II shows that 0.1% 13-cis-retinoic acid produced only a mild erythema and scaling, while 0.1% all-trans-retinoic acid produced severe erythema and scaling. The rabbits remained in good condition throughout the study.

TABLE II

10-Day Repeat Dose Dermal Irritation Study

| Treatment | Percent Concentration | N | Mean (Day 11) Erythema | Scaling |
|---|---|---|---|---|
| Vehicle | — | 6 | 0 | 0 |
| 13-cis-retinoic acid | 0.1 | 6 | 1.4 | 1.2 |
| Vehicle | — | 6 | 0.2 | 0.2 |
| all-trans-retinoic acid | 0.1 | 6 | 3.0 | 3.0 |

Descriptive Rating for Erythema and Scaling

| | |
|---|---|
| 0 to 0.4 | None |
| 0.5 to 1.4 | Mild |
| 1.5 to 2.4 | Moderate |
| 2.5 to 3.0 | Severe |

What is claimed is:

1. The method of treating non-inflammatory acne which comprises applying 13-cis-retinoic acid topically to the affected area in a concentration effective for the treatment of acne.

2. The method of claim 1 wherein the 13-cis-retinoic acid is applied in a carrier and the application is continued until the acne has subsided.

3. The method of claim 1 wherein the 13-cis retinoic acid is applied in a concentration from about 0.01 to 0.5 percent, by weight, of the topically applied composition.

4. The method of claim 3 wherein the concentration of 13-cis-retinoic acid in the composition is in the order of about 0.1 percent, by weight.

5. The method of claim 2 wherein the carrier is a water-miscible organic liquid.

6. The method of claim 5 wherein the carrier consists of a mixture of from about 10–90% by weight of an alcohol and 90–10% by weight of a glycol.

7. The method of claim 6 wherein the alcohol is ethyl alcohol and the glycol is propylene glycol.

8. The method of claim 7 wherein the carrier consists of 70% ethyl alcohol and 30% propylene glycol.

* * * * *

REEXAMINATION CERTIFICATE (852nd)

United States Patent [19]

Mezick

[11] B1 4,487,782

[45] Certificate Issued  May 3, 1988

[54] TOPICAL TREATMENT OF NON-INFLAMMATORY ACNE

[75] Inventor: James A. Mezick, East Brunswick, N.J.

[73] Assignee: Ortho Pharmaceutical Corporation, Raritan, N.J.

Reexamination Request:
No. 90/000,830, Aug. 7, 1985

Reexamination Certificate for:
Patent No.: 4,487,782
Issued: Dec. 11, 1984
Appl. No.: 362,356
Filed: Mar. 26, 1982

[51] Int. Cl.$^4$ .................................... A61K 31/20
[52] U.S. Cl. .................................... 514/559; 514/725; 514/859
[58] Field of Search ........................ 514/559, 859

[56] References Cited

U.S. PATENT DOCUMENTS

| | | | |
|---|---|---|---|
| 3,006,939 | 10/1961 | Pommer et al. | 260/413 |
| 3,729,568 | 4/1973 | Kligman | 424/318 |
| 3,882,244 | 5/1975 | Lee | 424/318 |
| 3,906,108 | 9/1975 | Felty | 424/318 |
| 3,932,665 | 1/1976 | Van Scott et al. | |
| 4,214,000 | 7/1980 | Papa | 424/289 |
| 4,322,438 | 3/1982 | Peck | |

FOREIGN PATENT DOCUMENTS

1335867 10/1973 United Kingdom.
1476717 6/1977 United Kingdom.

OTHER PUBLICATIONS

"Investigational Drug Brochure RO-43780 13-cis-Retinoic Acid", Div. of Medical Affairs, Hoffmann-LaRoche Inc., Nutley, N.J. 07110, undated.
Tentative Findings of the Advisory Review Panel on OTC Antimicrobial Drug Products, Information Copy, Acne Drug Products (Health and Human Services, Oct. 1980), pp. 43, 87–90, 289–291.
Frank, S. B., Acne: Update for the Practitioner (New York: Yorke Medical Books, 1979), pp. 250–256, 259–260.
Handbook of Nonprescription Drugs. Fifth Edition (American Pharmaceutical Association, Jan. 1977), pp. 317–318.
Balknap, B. S., MD, "Treatment of Acne with 5 Percent Benzoyl Peroxide Gel or 0.05 Percent Retinoic Acid Cream," CUTIS, vol. 23, Jun. 1979, pp. 856–859.
Federal Register: Topical Acne Drug Products for Over-the-Counter Human Use; Establishment of a Monograph (Rockville, MD: Food and Drug Administration, Mar. 23, 1982), pp. 12465–12468.
Federal Register: Topical Acne Drug Products for Over-the-Counter Human Use; Tentative Final Monograph (Rockville, MD: Food and Drug Administration; Jan. 15, 1985), pp. 2174–2175.
Stoughton, R. B., MD, "Topical Antibiotics for Acne Vulgaris," Arch Dermatol, vol. 115, Apr. 1979, pp. 486–489.
Rosen, T., MD, et al, "Topically Administered Clindamycin in the Treatment of Acne Vulgaris and Other Dermatologic Disorders," Pharmacotherapy, vol. 1, Dec. 1981, pp. 201–204.
Stoughton, R. B., MD, et al, "Topical Clindamycin in the Control of Acne Vulgaris," CUTIS, vol. 17, Mar. 1976, pp. 551–554.
Kligman, A. M., MD, et al, "Topical Vitamin A Acid in Acne Vulgaris," Arch Derm, vol. 99, Apr. 1969, pp. 469–476.
McGillis, T. J., MD, et al, "Topical Vitamin A Acid in the Management of Comedo Acne," CUTIS, vol. 7, Feb. 1971, pp. 144–150.
Cullen, S. I., MD, "Evaluation of Tretinoin in the Treatment of Acne Vulgaris," vol. 10, Dec. 1972, pp. 751–753.
Mandy, S., "Tretinoin in Acne Vulgaris," Pediatric Dermatology, vol. 17, 1975, pp. 174–176.
Peck, G. L., MD, et al, "Prolonged Remissions of Cystic and Conglobate Acne with 13-cis-Retinoic Acid," The New England Journal of Medicine, vol. 300, Feb. 15, 1979, pp. 329–333.
Jones, H., et al, "13-cis-Retinoic Acid and Acne," The Lancet, Nov. 15, 1980, pp. 1048–1049.
Romiti, N., "Use of the Aromatic Retinoid Ro 11-1430 for Acne Therapy," Pharmatherapeutica, vol. 2, 1978, pp. 82–84.
Peck, G. L., et al, "Treatment of Lamellar Ichthyosis and Other Keratinising Dermatoses with an Oral Synthetic Retinoid," The Lancet, Nov. 27, 1976, pp. 1172–1174.
Hixson, E. J., et al, "Comparative Subacute Toxicity of All-trans- and 13-cis-Retinoic Acid in Swiss Mice," Toxicology and Applied Pharmacology, vol. 44, 1978, pp. 39–40.
Merck Index, Ninth Edition (1976) p. 1060.
Physicians' Desk Reference, 29 Edition (1975) p. 831.
Pillsbury, D. M. et al, "A Manual of Dermatology" (1980), p. 125.
Summary of NDA 17-340 (Aug. 9, 1972).
Johnson & Johnson Brochure "Retin-A" (Sep. 1971, Aug. 1978, Aug. 1981).

*Primary Examiner*—Allen J. Robinson

[57] ABSTRACT

Topical treatment of non-inflammatory acne by the administration of 13-cis-retinoic acid is disclosed.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *